US00PP10748P

United States Patent [19]

Osiecki

[11] Patent Number: Plant 10,748

[45] Date of Patent: Jan. 5, 1999

[54] SPATHIPHYLLUM PLANT 'S16'

[75] Inventor: Marian W. Osiecki, Marianna, Fla.

[73] Assignee: Oglesby Plants International, Inc., Altha, Fla.

[21] Appl. No.: 859,466

[22] Filed: May 19, 1997

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

| | | | |
|---|---|---|---|
| P.P. 9,677 | 10/1996 | Osiecki | Plt./88.1 |
| P.P. 9,901 | 5/1997 | Osiecki | Plt./88.1 |
| P.P. 10,008 | 8/1997 | Osiecki | Plt./88.1 |
| P.P. 10,013 | 11/1997 | Osiecki | Plt./88.1 |

*Primary Examiner*—Howard J. Locker
*Assistant Examiner*—Kent L. Bell
*Attorney, Agent, or Firm*—Rothwell, Figg, Ernst & Kurz

[57] ABSTRACT

A new and distinct cultivar of Spathiphyllum is provided. The plant is medium to large size, full, symmetrical; suitable for production in a 15–25 cm pot from a single tissue culture produced microcutting; maintains proper growth habit and leaf shape at close pot spacing; grows very virorously; branches early and freely; flowers naturally early, abundantly and year-round producing good quality inflorescences from the onset of flowering; has thick, strong peduncles and large spathes with very little green coloration, held relatively close to foliage.

2 Drawing Sheets

SUMMARY OF THE INVENTION

This invention relates to a new and distinct Spathiphyllum cultivar characterized by the following combination of repeatedly observed traits:

1. Medium to large size,
2. full and symmetrical growth habit,
3. growth habit and leaf shape maintained at crowded pot spacing,
4. vigorous growth,
5. early and abundant branching,
6. early, abundant and year-round natural flowering,
7. good quality inflorescences from the onset of flowering,
8. thick, strong peduncles,
9. large spathes with very little green coloration, held relatively close to foliage;

and primarily selected for those characteristics being so selected from the progeny of the cross stated below in a cultivated area near Altha, Fla.

ORIGIN AND ASEXUAL REPRODUCTION

The new cultivar is a product of a planned breeding program carried out at Oglesby Plant Laboratories, Inc. near Altha, Fla. The female parent was a selected clone of Spathiphyllum 'Linda' (unpatented) and the male parent was a selected clone of Spathiphyllum 'Petite' (unpatented). The cross was made in 1991. The plant was selected in 1993 and has since been asexually reproduced by tissue culture in the vicinity of Altha, Fla. with the characteristics stated, found to be maintained through successive generations. The plant is a sibling of Spathiphyllum 'S2', which is described in co-pending U.S. Plant Patent Application Ser. No. 08/858,489.

This new cultivar has been identified as Spathiphyllum 'S16'. It is possible that other identification will be adopted in the trade, but the name selected will serve for the purposes hereof.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'S16' was approximately 11 months from planting two tissue culture produced microcuttings and was grown in a 15 cm pot.

In the photographs:

DETAILED DESCRIPTION OF THE NEW CULTIVAR

Figure 1:
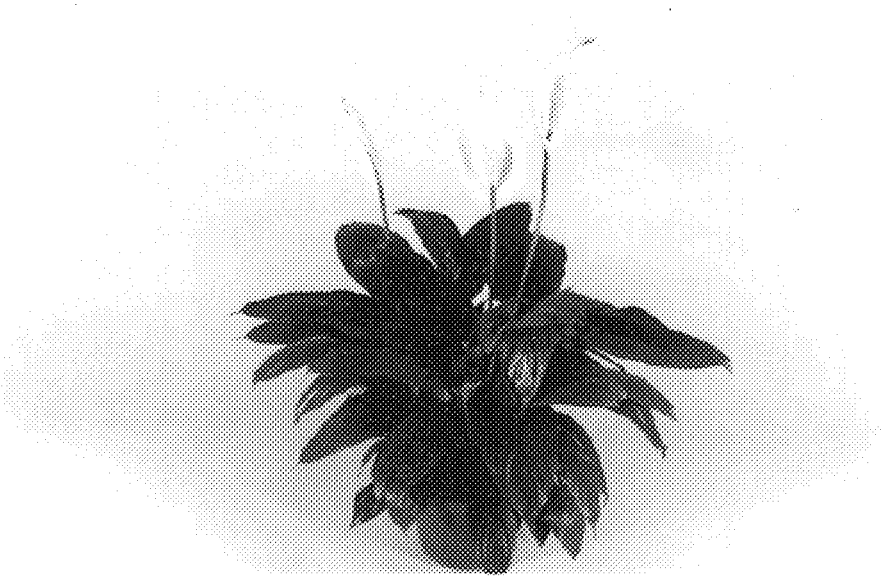
FIG. 1 depicts the whole plant.
Figure 2:
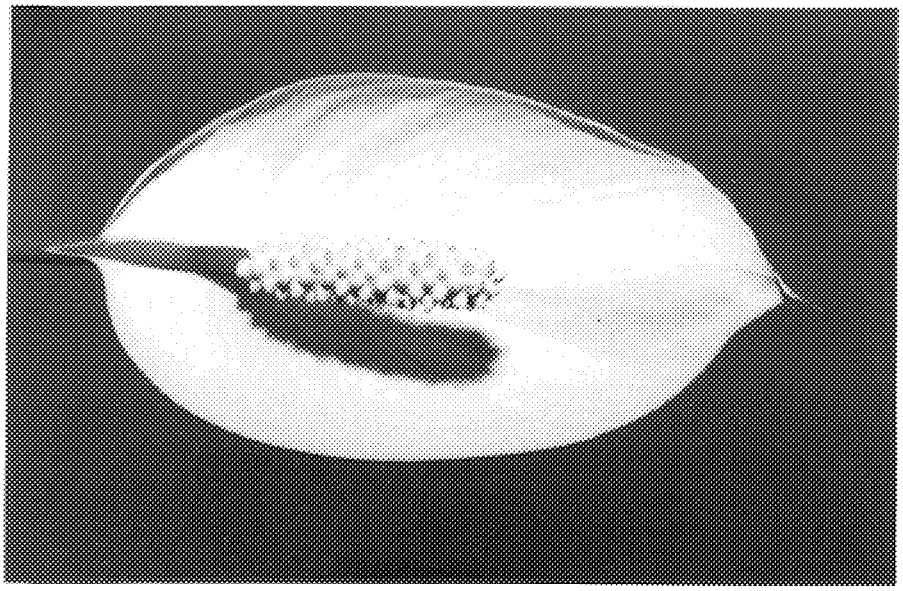
FIG. 2 illustrates the mature inflorescence.
Figure 3:
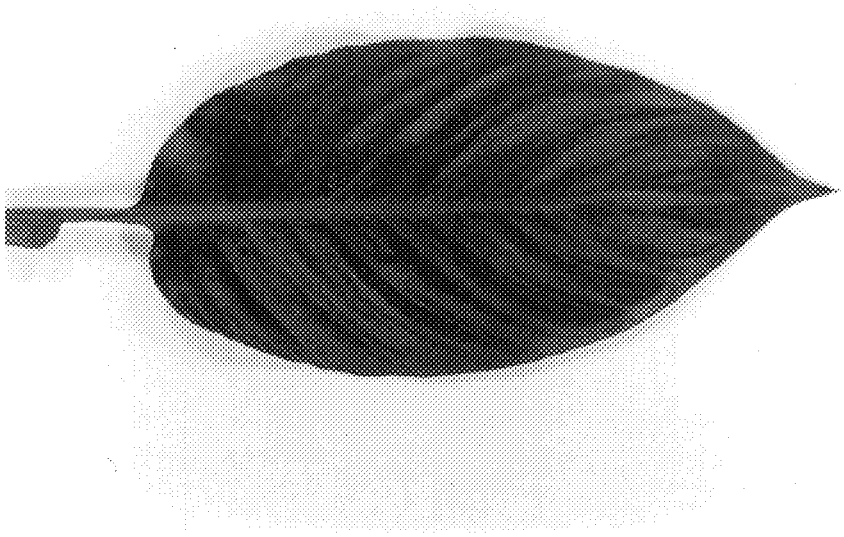
FIG. 3 illustrates the top of a mature leaf.
Figure 4:
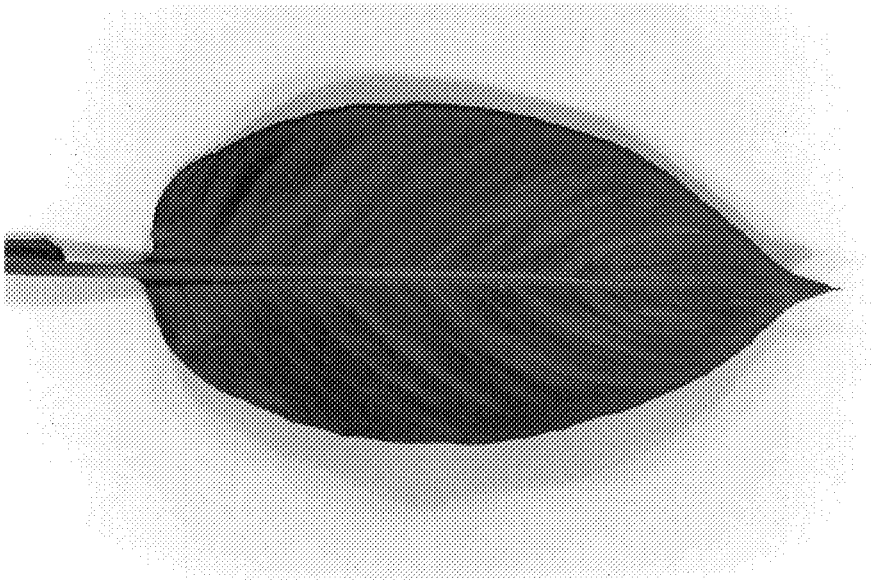
FIG. 4 illustrates the bottom of a mature leaf.

The following observations and measurements describe plants grown in Homestead, Fla. under shade house conditions. These observations and measurements were recorded in April 1997 from mature plants in 15 cm pots, about 11 months from planting two tissue culture produced microcuttings per pot. Fully developed organs on a dominant stem were used for measurements. Color values were determined on Apr. 7, 1997 under natural, indirect light of approx. 650–950 foot-candles. Color references are made to The R.H.S. Colour Chart, except where general color terms of ordinary significance are used. 'S16' has not been observed under all possible environmental conditions. The phenotype may vary with variations in environment and horticultural practices, such as temperature, light intensity, day length, fertilization, propagation method, etc., without any change in genotype.

Botanical classification: Spathiphyllum hybrid cultivar S16.

Parentage:

*Female parent.*—Selected clone of Spathiphyllum 'Linda'.

*Male parent.*—Selected clone of Spathiphyllum 'Petite'.

Propagation: Plant tissue culture.

Plant descriptions:

*Growth habit.*—Medium to large size, full, symmetrical, well branched with distinct main stem.

*Height.*—Foliage 30–36 cm, with spathes 48–55 cm.

*Maximum width.*—48–57 cm.

Petiole:

*Leaf supporting inflorescence.*—19.1–23.0 cm long, 4.2–5.0 mm in diameter immediately below geniculum. Geniculum 3.2–4.2 cm long, 4.6–5.2 mm in diameter at the base. Petiole wings 16.9–19.6 cm long.

*Leaf penultimate to leaf supporting inflorescence.*—13.0–16.7 cm long, 3.9–4.9 mm in diameter immediately below geniculum. Geniculum 2.6–3.3 cm long, 4.5–5.3 mm in diameter at the base. Petiole wings 9.8–14.0 cm long.

Leaf blade:

*Shape.*—Elliptic to ovate; width divided slightly unequally by midrib; tip acuminate with some cuspidate tendencies, often slightly curved; base obtuse, at times tending toward cuneate, especially in young shoots. Margin entire, slightly wavy.

*Size.*—Leaf supporting inflorescence: 20.7–23.7 cm long by 9.3–11.6 cm wide; length: width ratio 2.0–2.3:1. Leaf penultimate to leaf supporting inflorescence: 21.3–22.2 cm long by 9.6–11.5 cm wide; length: width ratio 2.0–2.2:1.

*Texture.*—Smooth, glossy.

*Veins.*—Well defined and sunken in the adaxial leaf surface.

*Color.*—Mature leaf: Adaxial: similar to 147A (yellow-green). Abaxial: similar to 147B with some resemblance to 137C (green). Newly unrolled leaf: Adaxial: more green than 146A (yellow-green), more yellow than 137A-B (green); Abaxial: slightly lighter than 147B.

Inflorescence:

*Arrangement.*—Spathes carried on thick, strong peduncles relatively close to foliage. Spathe length-:spadix length ratio 2.1–2.6:1.

Peduncle:

*Size.*—37.4–42.8 cm long; 5.8–6.8 mm in diameter immediately below spathe. Stipe 1.0–1.8 cm long, 5.2–5.9 mm in diameter. Approximately 4–5 cm below spathe peduncle thins abruptly by less than 1 mm and sometimes slightly bends.

*Color.*—Front: similar to 144A (yellow-green) near spathe with irregular, longitudinal, lighter (144B-C) streaks on stipe; proximally becomes darker — similar to 146A immediately below the zone of abrupt thinning. Back: more yellow than 137C (green) and more green than 146B (yellow-green) near spathe; proximally slightly darker — similar to but more green than 146A. Streaks on stipe usually less pronounced than in front.

Spathe:

*Shape.*—Elliptic with ovate tendencies; tip — acuminate with cuspidate tendencies, twisted, usually asymmetric; base cuneate to almost obtuse. Past maturity spathe often leans back from juncture with stipe exposing to view the entire spadix. Spathes on side shoots tend to be more elliptic, narrower and have more cuneate bases.

*Size.*—14.5–19.6 cm long, 8.0–10.4 cm wide, 1.9–2.3 cm deep; length:width ratio 1.6–2.0:1.

*Texture.*—Smooth, slightly glossy.

*Color.*—Bud: Lighter than 160D (greyed-yellow). Unrolled spathe: 155A (white) in front and a little lighter than 155A in the back. Green coloration on the back is confined to a narrow band along midrib and to the tip. From juncture with stipe distally the edges of the band are between 137B-C and 146A-B and the center is lighter (similar to 146B-D). The band tapers and in the distal half of the spathe appears as a fine line (similar to 146B-D) or in some spathes is partly absent. In the tip midrib is 146 A with some diffused 146B-C on both sides of the midrib. On the front the green coloration is limited to the tip, which is of a similar color as in back. Spathe remains white for up to 5 weeks following bud appearance above foliage and then gradually changes to a green color.

Spadix:

*Size.*—6.3–8.2 cm long; 1.7–1.8 cm in diameter.

*Flower density.*—Approximately 5–7 flowers per linear 2-cm in mid-portion of spadix.

*Color.*—Determined by the pistils color. 158B-C (yellow-white).

Botanical flower:

*Size and shape.*—Perianth only slightly visible between thick pistils. Pistil elliptic with acute tip; approximately 5 mm long and 2.5–3 mm in diameter; protrudes approximately 2–3 mm beyond perianth; stigmas relatively small. Stamen approximately 2 mm long and 1–1.5 mm wide, with reduced filament. Stamens firmly pressed against the pistil and not visible above perianth until pollen release, at which time anthers protrude beyond perianth.

*Color.*—Perianth, pistil and stamen all yellow-white (approximately 158B-D). Pollen abundant, color approximately 158A-C.

Roots: Main roots thick, fleshy. Relatively abundant fine lateral roots, white to cream.

Flowering: Flowers naturally in 12.5 cm pots, approx. 7–9 months from planting tissue culture produced microcuttings, producing good quality inflorescences from the onset of flowering. Three to four white spathes were present above foliage in a 15 cm pot, approximately 11 months from planting two microcuttings per pot.

Disease and insect resistance: No unusual susceptibility to diseases or insects noted to date.

Comparison with Known Cultivars:

The new cultivar can be compared to known cultivars 'Viscount' (unpatented) and 'Petite' (unpatented). 'S16' is distinguished from both cultivars by its fuller growth habit; more vigorous growth; earlier and more abundant branching; earlier and more abundant natural flowering; better quality of first inflorescences; thicker and stronger peduncles; larger spathes; lighter foliage. 'S16' is further distinguished by its leaf blades being smaller than those of 'Viscount', but wider than those of 'Petite'. The new cultivar can also be compared to the sibling cultivar 'S2', which is described in co-pending U.S. Plant Patent Application Ser. No. 08/858,489. 'S16' is distinguished from 'S2' by its more abundant branching; its fuller and less upright growth habit; slightly lighter green leaves that are more ovate and wider in proportion to their length and have more obtuse bases; by the spathes that are situated slightly nearer to foliage, are slightly more ovate and have slightly more obtuse bases.

I claim:

1. A new and distinct cultivar of Spathiphyllum plant named 'S16', substantially as described and illustrated herein, characterized particularly as to novelty by its medium to large size; full and symmetrical growth habit; vigorous growth; early and abundant branching; early, abundant and year-round natural flowering; large spathes with limited green coloration, held on thick, strong peduncles relatively close to foliage.

* * * * *